United States Patent
Kotsbak

(10) Patent No.: US 10,222,333 B2
(45) Date of Patent: Mar. 5, 2019

(54) METHOD AND APPARATUS FOR DETECTING MOLECULES

(75) Inventor: Jarle Kotsbak, Trondheim (NO)

(73) Assignee: GENESEQUE AS, Trondheim (NO)

( * ) Notice: Subject to any disclaimer, the term of this patent is extended or adjusted under 35 U.S.C. 154(b) by 96 days.

(21) Appl. No.: 13/258,219

(22) PCT Filed: Feb. 24, 2010

(86) PCT No.: PCT/GB2010/000324
§ 371 (c)(1),
(2), (4) Date: Sep. 21, 2011

(87) PCT Pub. No.: WO2010/109159
PCT Pub. Date: Sep. 30, 2010

(65) Prior Publication Data
US 2012/0015833 A1   Jan. 19, 2012

(30) Foreign Application Priority Data
Mar. 23, 2009 (GB) .................................. 0904934.7

(51) Int. Cl.
- *C12Q 1/68* (2018.01)
- *G01N 21/64* (2006.01)
- *G01N 21/25* (2006.01)
- *G01N 33/543* (2006.01)

(52) U.S. Cl.
CPC ....... *G01N 21/6454* (2013.01); *G01N 21/253* (2013.01); *G01N 33/54313* (2013.01); *G01N 33/54393* (2013.01)

(58) Field of Classification Search
USPC ........................................................ 359/566
See application file for complete search history.

(56) References Cited

U.S. PATENT DOCUMENTS

| | | | |
|---|---|---|---|
| 5,599,675 A | 2/1997 | Brenner | |
| 5,674,698 A * | 10/1997 | Zarling | G01N 33/588 422/504 |
| 5,714,330 A | 2/1998 | Brenner et al. | |
| 5,843,651 A | 12/1998 | Stimpson et al. | |
| 5,981,297 A | 11/1999 | Baselt | |

(Continued)

FOREIGN PATENT DOCUMENTS

| | | |
|---|---|---|
| EP | 0106873 B1 | 1/1986 |
| WO | 2005005951 A2 | 1/2005 |

OTHER PUBLICATIONS

Aytru et al, Journal of Immunological Methods, 2006, 314, 21-29.*
Myers and Lee, Lab Chip, 2008, 8, 2015-2031.*
Christodoulides et al., Lab Chip, 2005, 5, 261-269.*
Ymeti et al, Nano Letters, 2007, 7, 2:394-397.*

(Continued)

*Primary Examiner* — Betty J Forman
(74) *Attorney, Agent, or Firm* — Cantor Colburn LLP

(57) ABSTRACT

The present disclosure is directed to a method of detecting a molecule attached to a surface comprising detecting a bead attached to the molecule. The method may be used for the detection of single molecules and the surface shape may be adapted to receive beads. The disclosure further describes an apparatus for detecting the presence of a molecule having a bead attached thereto comprising a surface adapted to detect a bead wherein the shape of the surface is configured to receive and retain a bead. Kits comprising the apparatus are provided and a use of the apparatus for detecting a bead or a molecule attached thereto is also described.

10 Claims, 7 Drawing Sheets

Specification includes a Sequence Listing.

(56) References Cited

U.S. PATENT DOCUMENTS

| | | | |
|---|---|---|---|
| 7,323,305 | B2 | 1/2008 | Leamon et al. |
| 2003/0215844 | A1 | 11/2003 | Chapsky et al. |
| 2003/0215891 | A1 | 11/2003 | Bickel et al. |
| 2005/0059030 | A1 | 3/2005 | Bao et al. |
| 2005/0214863 | A1* | 9/2005 | McDevitt ............ B01J 19/0046 435/7.1 |
| 2005/0244863 | A1 | 11/2005 | Mir |
| 2005/0250094 | A1 | 11/2005 | Storhoff et al. |
| 2006/0084069 | A1* | 4/2006 | Chan et al. ....................... 435/6 |
| 2008/0037008 | A1 | 2/2008 | Shepard et al. |
| 2008/0220411 | A1* | 9/2008 | McNaughton ... G01N 33/54313 435/5 |
| 2008/0221432 | A1 | 9/2008 | Zhou |
| 2009/0048124 | A1 | 2/2009 | Leamon et al. |
| 2009/0187350 | A1* | 7/2009 | Chau et al. ..................... 702/19 |
| 2010/0035252 | A1 | 2/2010 | Rothberg et al. |

OTHER PUBLICATIONS

Adams et al., Sensors and Actuators A, 104, 2003, 25-31.*
Craighead, Nature, vol. 442, Jul. 2006, p. 387-393.*
Lehmann et al. 2009. Actuation and Detection of Magnetic Microparticles in a Bioanalytical Microsystem with Integrated CMOS Chip. In De Mecheli et al. Nanosystem Design and Technology. Chapter 4. pp. 85-102. DOI 10/1007/978-1-4419-0255-9_4.*
Sakata et al, Langmuir, 2007, 23 (5), pp. 2269-2272.*
Ozcan et al "Ultra wide-field lens-free monitoring of cells on-chip", Lab on a Chip, 8: 98-106.*
"Photonfocus CMOS Sensors"; retrieved from the internet: URL:http://photonfocus.com/html/eng/products/prodList.php?cat+CMOS+Sensors; 1 page; Sep. 23, 2008.
"Removal of the Standard Glass Cover from CCD/CMOS Image Sensors"; retrieved from the internet: URL:http://www.eureca.de/english/optoelectronics_glass_cover.html; Mar. 20, 2008.
Wang et al.; "A Frequency-Shift CMOS Magnetic Biosensor Array with Single-Bead Sensitivity and No External Maganet"; from Solid-State Circuits Conference—Digest of Technical Papers; pp. 438-439, 439a; Feb. 11, 2009.
Baudot, et al.; "Photon Detection with CMOS Sensors for Fast Imaging"; Nuclear Instruments and Methods in Physics Research; 604; pp. 111-114; (2009).
Charbon, Edoardo; "Towards Large Scale CMOS Single-Photon Detector Arrays for Lab-on-Chip Applications"; J. Phys. D: Appl. Phys.; 41; 9 pages; (2008).
Edelstein et al.; "The Barc Biosensor Applied to the Detection of Biological Warfare Agents"; Biosensors and Bioelectronics; 14; pp. 805-813; (2000).
International Search Report; International Application No. PCT/GB2010/000324; International Filing Date Feb. 24, 2010; Earliest Priority Date Mar. 23, 2009; dated Jun. 16, 2010; 5 pages.
Ji, et al.; "Contact Imaging: Simulation and Experiment"; IEE Transactions on Circuits and Systems—I; Regular Papers; 54(8); pp. 1698-1710; (2007).
Lehmann et al.; "Microparticle Photometry in a CMOS Microsystem Combining Magnetic Actuation and in situ Optical Detection"; Sensors and Actuators; B 132; pp. 411-417; (2008).
Mallard, et al.; "Opto-electronic DNA Chip: High Performance Chip Reading with an All-Electric Interface"; Biosensors and Bioelectronics 20(9); pp. 1813-1820; (2005).
Su et al.; "High-Throughput Lensfree Imaging and Characterization of a Heterogeneous Cell Solution on a Chip"; Biotechnology and Bioengineering; 102(3); pp. 856-868; (2009).
Tokuda et al.; "Optical and Electrochemical Dual-Image CMOS Sensor for On-Chip Biomolecular Sensing Applications"; Sensors and Actuators; 135; pp. 315-322; (2007).
Written Opinion; International Application No. PCT/GB2010/000324; International Filing Date Feb. 24, 2010; Priority Date Mar. 23, 2009; dated Jun. 16, 2010; 9 pages.
Antibody Microarray; Wikipedia; http://en.wikipedia.org/wiki/antibody microarray; 3 pages; accessed Dec. 18, 2008.
Aytur et al.; "A Novel Magnetic Bead Bioassay Platform Using a Microchip-Based Sensor for Infectious Disease Diagnosis"; Journal of Immunological Methods; 314; pp. 21-29; (2006).
Chemical Compound Microarray; Wikipedia; http://en.wikipedia.org/wiki/Chemical compound microarray; 2 pages; accessed Dec. 18, 2008.
DNA Microarray; Wikipedia; http://en.wikipedia.org/wiki/DNA microarray; 12 pages; accessed Dec. 18, 2008.
Gunderson et al.; "Mutation Detection by Ligitation to Complete n-mer DNA Arrays" Denome Research; 8(11); pp. 1142-1153; (1998).
Image Sensor; Wikipedia; http://en.wikipedia.org/wiki/Image sensor; 8 pages; accessed Dec. 18, 2008.
Ju et al.; "Four-color DNA Sequencing by Synthesis Using Cleavable Fluorescent Nucleotide Reversible Terminators"; PNAS; 103(52); pp. 19635-19640; (2006).
Lavery et al.; "Structure and Mechanics of Single Biomolecules: Experiment and Simulation"; J. Phys. Condens. Matter; 14; pp. R383-R414; (2002).
LeBlanc et al.; "Development of a Magnetic Bead Microarray for Simultaneous and Simple Detection of Four Pestiviruses"; Journal of Virological Methods; 155; pp. 1-9; (2009).
Li et al.; "Detection of Single Micron-Sized Magnetic Bead and Magnetic Nanoparticles Using Spin Valve Sensors for Biological Applications"; Journal of Applied Physics; 93(10); pp. 7557-7559; (2003).
MicroRNA; Wikipedia; http://en.wikipedia.org/wiki/MMChip; 24 pages; accessed Dec. 18, 2008.
Mulvaney et al.; "Rapid, Femtomolar Bioassays in Complex Matrices Combining Microfluidics and Magnetoelectronics"; Biosensors and Bioelectronics; 23; pp. 191-200 (2007).
Mulvaney et al.; "Attomolar Protein Detection in Complex Sample Matrices With Semi-Homogeneous Fluidic Force Discrimination Assays"; Biosensors and Bioelectronics; 24; pp. 1109-1115; (2009).
Point-of-Care Technologies 2008; Medical Device Link http://www.devicelink.com/ivdt/archive/08/07/008.html; 3 pages; accessed Dec. 18, 2008.
Protein Arrays Resource Page; http://www.functionalgenomics.org.uk/sections/resources/protein_arrays.htm; 14 pages; accessed Dec. 18, 2008.
Protein Microarray; Wikipedia; http://en.wikipedia.org/miki/Protein microarray; 5 pages; accessed Dec. 18, 2008.
Stahl et al.; "Visual DNA—Identification of DNA Sequence Variations by Bead Trrapping"; Genomics; 90; pp. 741-745; (2007).
Steinberg et al.; "Strategies for Covalent Attachment of DNA to Beads"; Biopolymers; 73; pp. 597-605; (2004).
Tokuda et al.; "A CMOS Optical/Potential Image Sensor with 7.5 um Pixel Size for On-Chip Neural and DNA Spot Sensing"; Proceedings of the 2005 IEEE, Engineering in Medicine and Biology 27 Annual Conference, Shanghai, China, Sep. 1-4, 2005.
Xu et al.; "Protein and Chemical Microarrays—Powerful Tools for Proteomics"; Journal of Biomedicine and Biotechnology; 5; pp. 257-266; (2003).
Photonfocus CMOS Sensors; retrieved from the internet: URL:http://photonfocus.com/html/eng/products/prodList.php?cat=CMOS+Sensors; Feb. 4, 2009.
Removal of the Standard Glass Cover from CCD/CMOS Image Sensors; Retrieved from the internet: URL:http://www.eureca.de/english/optoelectronics_glass_cover.html; last updated Mar. 30, 2008.
Su, Ting-Wei et al.; "High-Throughput Lensfree Imaging and Characterization of a Heterogeneous Cell Solution on a Chip"; Biotechnology and Bioengineering; 102(3); pp. 856-868; (2009).
Wang, et al.; "A Frequency-shift CMOS Magnetic Biosensor Array with Single-bead Sensitivity and No External Magnet"; IEEE Solid-State Circuits Conference—Digest of Technical Papers, 2009. ISSCC 2009. IEEE International, IEEE, Piscataway, NJ, USA, Feb. 11, 2009.
EP Search Report; Application No. 10 705 912.3-1405; dated Sep. 6, 2013; 14 pages.

* cited by examiner

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial sequence
<220> FEATURE:
<223> OTHER INFORMATION: primer

<400> SEQUENCE: 1
agcggataac aatttcacac agga                                            24

<210> SEQ ID NO 2
<211> LENGTH: 21
<212> TYPE: DNA
<213> ORGANISM: Artificial sequence
<220> FEATURE:
<223> OTHER INFORMATION: primer

<400> SEQUENCE: 2
aaacgacggc cagtgccaag c                                               21
```

METHOD AND APPARATUS FOR DETECTING MOLECULES

FIELD OF THE INVENTION

The present invention relates to the field of molecule detection and in particular to the field of microarray technology for the detection of molecules.

BACKGROUND

Many different methods are known in the art which can be used for the detection of molecules. In particular, microarray technology has evolved into a powerful tool for the detection of many different types of molecule e.g. DNA, RNA, protein, antibodies and chemical compounds. Microarrays have been developed to study gene expression, to identify gene mutations, aneuploidy and polymorphisms and to identify protein:protein interactions, to name only a few uses. This technology has proven to be an important technique, particularly for research and for diagnostics.

Microarray chips generally consist of a collection of microscopic molecule spots attached to a solid surface such as glass, silicon or a nylon membrane. Target molecules in a sample can be assessed by determining their binding pattern to molecules on a particular microarray. Target molecules are usually fluorescently labelled and a microarray can therefore be read and a target molecule detected by determining the presence (and level) of fluorescence at each molecule spot on the microarray, which corresponds to the presence (and amount) of target molecule present in a sample. The use of fluorescent labels however requires the use of fluorescence scanners which although result in accurate and sensitive methods, are expensive. The requirement for expensive scanners has prevented the use of microarrays as a routine tool in research and in diagnostics.

Additionally, it is not usually possible to detect single molecules using fluorescent labelling and microarray technology. Particularly in the case of nucleic acid detection it is usually necessary to carry out an amplification step prior to applying a sample to a microarray. Fluorescent scanners/detectors are not usually sensitive enough to detect the presence of a single fluorescent label and hence the presence of a single molecule.

Mallard et al (Biosensors and Bioelectronics, 20, 1813-1820, 2005) developed a CMOS photodetector array as a solid support for a DNA chip where detection was by means of chemiluminescence. Although this system did not require the use of an expensive detector or fluorescent scanner, it again was not sensitive enough to enable the detection of a single molecule. Tokuda et al (Proceedings of the 2005 IEEE, Engineering in Medicine and Biology 27th Annual Conference, Shanghai, China, Sep. 1-4 2005, 7269-7272) further developed a CMOS image sensor for bioimaging applications in which fluorescence imaging was used.

Chan et al (US2006/0084069) developed an integrated circuit optical detector as a solid support for an array where the presence of a target was detected by receiving and sensing optical signals from a nanoparticle label. However, although this method did not require the use of an expensive scanner or detector, the optical detection of very small nanoparticles was not sensitive enough to detect single molecules.

Thus there exists a need for an array molecule detection system which is capable of detecting single molecules and which does not rely on the use of expensive scanners or detectors.

SUMMARY

The present invention addresses the problem and enables the detection of single molecules without the need for expensive external equipment by using an array which is provided with one or more light sensitive elements, together with a bead label for the molecule which is of sufficient size to prevent the one or more light sensitive elements from receiving light when the bead is present and bound to a single-molecule attached to the array. Thus, the size of the label used may correspond to the size of each light sensitive element on the array in order to allow the detection of single molecules in the present invention.

Alternatively viewed, as discussed below in detail, the bead label has a minimum size which is linked to the size of each light sensitive element and typically for example the bead should be at least 1 µm in diameter.

Figure 1:
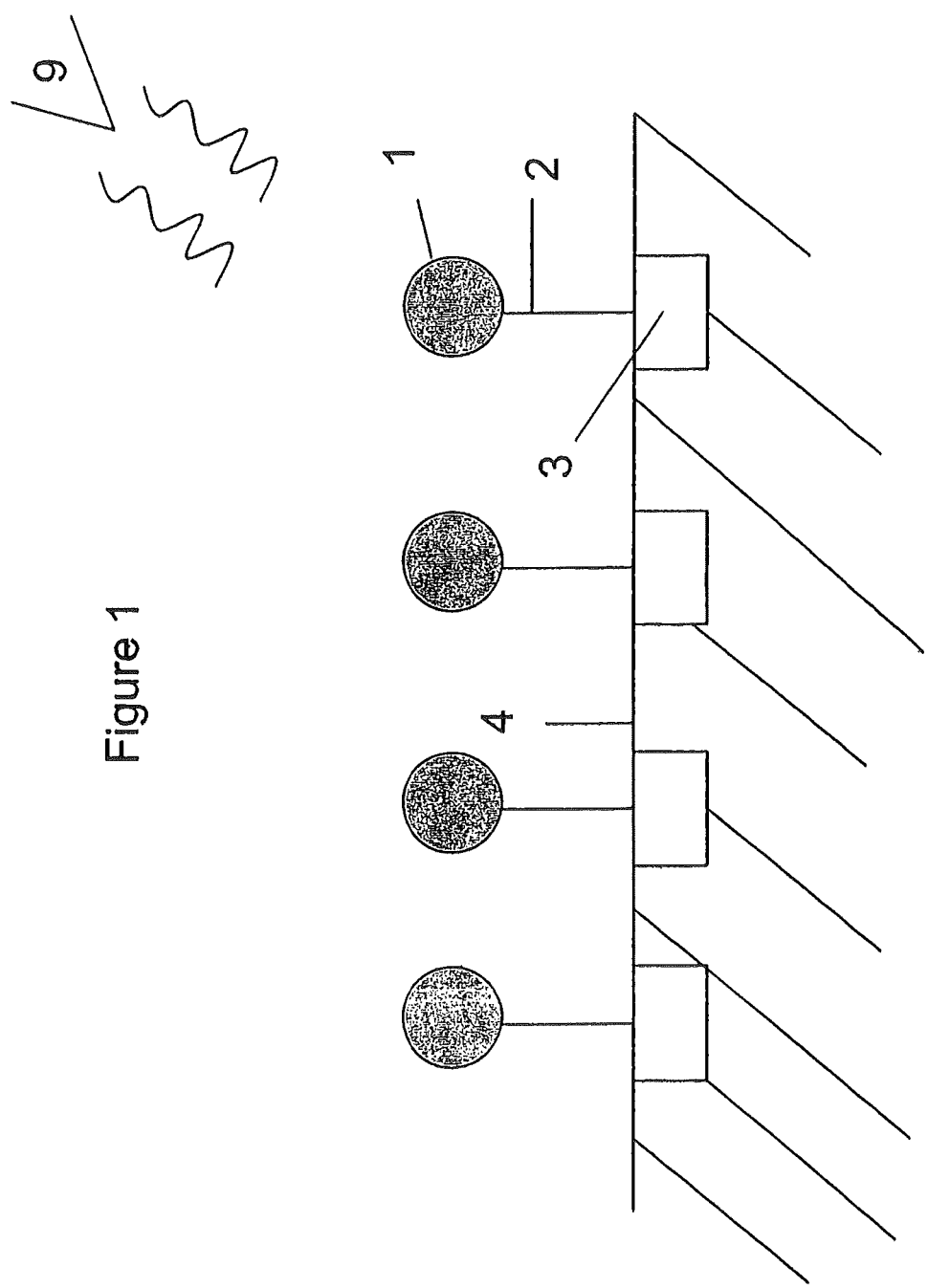
FIG. 1 shows a schematic view of the method of the invention in practice.

Embodiments of the invention will now be described, by way of example only, with reference to the accompanying drawings.

DETAILED DESCRIPTION

According to a first aspect, the invention thus provides a method of detecting a molecule attached to a surface the method comprising detecting a bead attached to said molecule, wherein said surface is provided with one or more light sensitive elements and wherein each light sensitive element is arranged to detect a bead adjacent thereto.

As discussed above, in order to detect single molecules, bead labels of a particular size are used and generally beads are chosen which correspond in size to the size of each light sensitive element on the surface. In this way a single bead attached to a single molecule at a particular position can be detected by a light sensitive element.

Thus, the invention also provides a method of detecting a molecule attached to a surface the method comprising detecting a bead attached to said molecule, wherein said surface is provided with one or more light sensitive elements, wherein each light sensitive element is arranged to detect a bead adjacent thereto and wherein said bead is (i) of a size which corresponds to the size of said one or more light sensitive elements or (ii) is at least 1 µm in diameter, allowing the detection of a single molecule attached to the surface.

Hence, the presence or absence of a molecule attached to a surface can be detected by detecting the presence or absence of a bead which is attached to the molecule. The one or more light sensitive elements provided on or within the surface are capable of outputting a signal which is dependent on the presence or absence of a bead and the signal provided from each light sensitive element will therefore indicate whether a bead and hence a molecule bound to the bead is present. The bead is thus itself directly detected by said one or more light sensitive elements and not by any external scanners, cameras or other devices. Although the beads may be arranged to emit light which can be detected by a light sensitive element (e.g. it may be fluorescent), this is not necessary. Rather, it is preferred that the beads are detected when they block light from reaching the light sensitive element in question. Thus, they effectively cast a shadow on the element. The light source may simply be ambient light, but in order to provide greater reliability, it is preferred that a dedicated light source be provided. This may provide light at any frequency (ies) to which the detector is sensitive but preferably it is in the visible range of 350-750 nm. By illuminating the surface, the detection of any shadows created by the presence of beads or the obstruction of light from the light sensitive elements can be detected more easily. It will be appreciated that a much greater difference in signal will be generated between the presence and absence of a bead when the surface is illuminated and hence illumination by using an external light source results in a more sensitive method.

To prevent external light sources from affecting results, preferably the light sensitive elements are shielded from external light by a suitable housing.

It will be seen that the light sensitive elements are therefore capable of measuring the amount of light received by the surface which can determine the presence or absence of a bead or the number of beads present. A bead can be detected by an individual light sensitive element or by a group of light sensitive elements, depending on the size of the beads, the light sensitive elements and the distance of the beads from the surface. As discussed previously, a single bead and hence a single molecule can be detected using the method of the invention since generally the size of the bead will correspond to the size of each light sensitive element. Hence, it is possible that an individual light sensitive element can detect a bead or that 2, 3, 4 or more light sensitive elements can detect a bead depending on the bead and element sizes. The amount of light detected by each light sensitive element and hence the signal output from the light sensitive elements when no beads are present can be used as a reference point against which other measurements can be compared. A reduction in light (i.e. created by the shadow of bead) received by a light sensitive element will result in the output of a signal which differs from that outputted when beads are absent. As discussed below, the amount of light received by each light sensitive element when a bead is present will depend upon various factors, including the bead size, the size of each light sensitive element, the length of the molecule attached to the surface and also on the number of beads present.

Alternatively viewed, the invention provides a method of detecting a molecule attached to a surface provided with one or more light sensitive elements said method comprising detecting said molecule by detecting a bead attached thereto wherein said bead is detected by a light sensitive element or a group of light sensitive elements provided by said surface.

Thus, for the detection of a single molecule the bead should be of a size which corresponds to the size of a light sensitive element, such that a single bead is able to block light from reaching the light sensitive element.

As discussed further below, the method of the invention may further comprise a step of attaching the molecule to the surface prior to the detection step and/or a step of attaching the bead to the molecule. Additionally, unbound beads may be removed prior to the start of the detection method. A step of cleaving the beads from the molecule and from the surface may be carried out after detection of the bead.

Thus, the present inventors have proposed a detection method whereby single molecules can be detected using image sensors without the need for expensive detection scanners. In this regard, the inventors have found that beads can be detected on image chips. The detection of molecules using image chips will therefore be possible using bead labels. Beads are larger and easier to detect than fluorescent labels or chemiluminescence or even nanoparticles and hence using a detection method with bead labelled molecules will allow the detection of small amounts or single molecules. The bead labels may be of a particular minimum size to allow the detection of a single molecule and as previously discussed, the size of the bead may correspond to the size of a light sensitive element. Additionally and advantageously, in contrast to fluorescent labels or the enzymes required to induce chemiluminescence, unbound bead labels can be easily removed from the sample at any point during the method e.g. by using a magnet for magnetic beads. The removal of excess label in this way can reduce the washing steps which are required during the method and the excess bead labels can be reused in a subsequent reaction. Importantly, since the image chips are capable of detecting beads, the method and apparatus proposed in the present invention will further circumvent the requirement for expensive scanners and detectors.

The inventors have therefore identified an extremely sensitive and inexpensive detection method for molecules and particularly single molecules which has not been suggested or alluded to in the prior art.

The term "bead" as used herein refers to a microparticle which is typically, but not necessarily, a spherical solid support. The bead is not a nanoparticle e.g. a nano-metallic particle or a gold cluster. Such nano-particles are understood in the art to have a very small size and are typically less than 2 nm in diameter. Such labels are not encompassed within the term "bead" as used herein. The bead used generally has a size which corresponds to the size of the light sensitive element provided on the surface and thus the surface and beads to be used in the methods of the invention are generally selected together i.e. a particular size combination may be chosen. As discussed above, in order for the methods to be capable of detecting single molecules, the bead labels used generally have a minimum size which corresponds to the size of the light sensitive elements on the surface. The bead can be made from any material which allows the formation of a suitable support as described in more detail below. The bead and the surface are different entities.

The "surface" is preferably provided with a plurality of light sensitive elements arranged to form an array. The light sensitive elements may be on or form the outer layer of the surface or may be comprised within the surface e.g. may be present beneath one or more other material layers. Arrays of light sensors or of light sensitive elements are well known in the art and include charged coupled devices e.g. of the type used in cameras or CMOS active pixel sensors. In the present invention, modifications may be made to such CCD or CMOS image chips as discussed further below. The surface may be the substrate of such a device. Thus, the surface provides one or more light sensitive elements and preferably external cameras (e.g. CCD) or sensors not provided by the surface are not used or required for molecule detection.

The molecule to be detected may be attached to or placed above the one or more light sensitive elements present in or on the surface to enable the generation of an output from the attached bead. One or more molecules may be associated with one or more of the light sensitive elements e.g. one or several molecules may be associated with each light sensitive element or group of light sensitive elements but typically each light sensitive element or element group will have only one molecule type associated therewith (but one or more copies of that molecule type may be present). Preferably, a single molecule may be associated with a light sensitive element or a group of elements and may be detected using the method of the invention.

The bead may cast a shadow on the surface and on a light sensitive element or a group of light sensitive elements when the bead is present and hence reduce the amount of light received by the light sensitive element(s). For example, the bead may reduce the amount of light received by the light sensitive element(s) by from about 10-100%, e.g. particularly from 20, 30, 40, 50, 60, 70, 80 or 90%. In one aspect, the bead may prevent all light from being received by the light sensitive element. It will be appreciated that the output provided will be dependent on the size of bead used, the size of the individual light sensitive elements present on the surface and the distance from which the bead is tethered from the surface. Therefore, a bead which is the same size or larger than a light sensitive element may prevent most light from falling on the light sensitive element. Each light sensitive element and bead size combination may be calibrated by measuring the signal output when any number of beads are present or attached to each light sensitive element.

It is possible for a particular bead size to be chosen depending on the size of the light sensitive elements in or on the surface. Particularly, for the detection of a single molecule, a bead may be selected which corresponds to the size of the one or more light sensitive elements in or on the surface. A bead which "corresponds" to the size of one or more light sensitive elements is one which when attached to the surface may reduce the amount of light received by said one or more light sensitive elements by at least 50, 60, 70, 80 or 90%. Such beads typically have a diameter which is at least 30, 40, 50, 60, 70, 80, 90 or 95% of the width and/or breadth (or diameter) of a light sensitive element or a group of light sensitive elements. Thus, if a bead is to be detected by a single light sensitive element then that bead size (i.e. diameter) may correspond to the size of that light sensitive element e.g. may be at least 30, 40, 50, 60, 70, 80 or 90% of the width or breadth (or diameter) of the light sensitive element. Alternatively, if the bead is to be detected by a group of light sensitive elements e.g. more than 1 light sensitive elements then the bead size (diameter) may correspond to the size of the group of light sensitive elements e.g. may be at least 30, 40, 50, 60, 70, 80 or 90% of the width and/or breadth (or diameter) of the group of light sensitive elements. Typically, the bead may have a minimal size (diameter) of 1 μm i.e. is at least 1 μm in diameter. Such a size generally allows the detection of single molecules in the present invention. For example, 1 μm diameter beads may be used in combination with 1.75×1.75 μm light sensitive elements or 2.8 μm diameter beads may be used with 3.2×3.2 μm light sensitive elements.

Additionally, the light sensitive elements may detect the number of beads bound to a particular position or a particular molecule by detecting the amount of light received at that position. In this aspect, it will be necessary to use beads which are smaller than the individual light sensitive elements or group of light sensitive elements. Hence, the beads should be smaller than the area covered by one particular type of molecule attached to a light sensitive element or a group of light sensitive elements. In this instance, the detection of the number of beads may indicate the concentration of a particular molecule type at a position. Preferably, the incubation time may be limited.

Coloured beads may be used in the above described method which may be detected by the one or more light sensitive elements when illuminated with light. Particularly, the coloured beads may be fully transparent or partially transparent e.g. the beads may contain a non-transparent nucleus which may be magnetic (e.g. paramagnetic). Different colour beads may be detected on the surface by each light sensitive element by illuminating the surface with light of different colours. Hence, two, three, four or more different colour beads can be detected by the surface by illumination with different colour light. The surface may be capable of providing an output for each colour bead/light colour combination applied. The intensity of light detected may again be indicative of the number of beads bound to each light sensitive element and hence may indicate the quantity or concentration of the molecule attached at that position.

The light sensitive elements are able to convert the light energy received into voltage which may then be converted into digital data e.g. by an integrated circuit. In this way, the surface comprising the elements is itself capable of detecting the presence of a molecule by detecting a bead attached to that molecule. There is no need for external expensive equipment to be employed to detect the presence of the signal or label attached to the molecule. The surface itself is able to detect the molecule.

As noted above, known CMOS or CCD detectors are suitable for use in the present invention. For example, image chips of the sort used in mobile phones can be used in the present methods. In a preferred aspect, the surface of, for example a CMOS or CCD image sensor form the surface of the invention.

The CMOS photodetector (or Active Pixel Sensor) has been developed essentially for consumer camera applications e.g. in webcams or mobile phones. Two variants of this detector are available, namely the bare die variant or a variant with the die packaged with a protective glass and bonded to pads that are connected to the external pads made for soldering. The bare die variant may be used directly in the present invention, whereas the packaged die variant CMOS photodetector may be modified by removing the glass lid. For both variants, it may be preferable to remove the layers of microlenses and colour filters which usually cover the pixels in order that molecules may be arrayed on the surface of the photoelements or pixels. CMOS or other photodetectors may be manufactured without the additional microlens/filter layers present which are required for use in mobile phones, for direct use in the present invention. Hence, particularly adapted CMOS image chips may be used in the invention.

Particularly, the surface may comprise at least 3 Megapixels (2048×1536 light sensitive elements) or at least 4, 5, 6, 7, 8, 9, 10, 11 or 12 Mpixels. Using standard deposition processes, it may be possible to deposit and detect molecules associated with at least 1, 5, 10, 15, 20, 25, 30, 35 or 40% of the light sensitive elements. The light sensitive elements or pixels present on an image chip are usually the same size, although differences in size may occur. The pixels may be for example in the range of 0.5×0.5 μm to 10×10 μm, for example 1×1 μm, 2×2 μm, 3×3 μm, 4×4 μm, 5×5 μm or 6×6 μm and particularly, the pixels may be 1.75×1.75 μm or 3.2×3.2 μm.

Modifications may additionally be made to the surface e.g. to that of the image chips to assist in the attachment of molecules to the surface. Particularly, the image chips may be coated with gold or may be modified to have silan or antidigoxigenin groups attached. The thickness of the layer of gold which may be used is not critical provided that too much light is not blocked from reaching the light sensitive elements. For example, gold layers may range from 5 to 50 nm. Methods of modifying surfaces in such ways are known in the art. Gold coating may be carried out by vacuum deposition or by deposition from a highly concentrated gold solution. Aminosilane modification of surfaces can be achieved by for example incubating the surface with 5% aminopropyltriethoxysilane (CAS:019-30-2) in dry acetone for one hour at room temperature. Aminosilane surfaces can be used as is, to add desired molecules directly, or can be further modified by adding a bifunctional crosslinker, such as m-maleididibenzoyl-N-hydroxysulfo-succinimide ester in order to be able to bind molecules to the surface. Antidigoxigenin modification is achieved by first priming the surface with a poly-1 lysin solution (10% poly-1 lysin v/v and 10% PBS), and then by adding antidigoxigenin 1:100 in INVITROGEN™ CNB0011 coating buffer A.

Additionally, the surface of the invention may be equipped with a flow cell which allows fluid flow to and from the surface. Hence, the flow cell can be used to apply a sample or the molecule to the surface and/or to apply beads. Preferably, therefore, the sample or molecule(s) is not applied to the surface by pipetting. Further, the surface may be arranged with a reader which is capable of detecting and reading the signals from each of the light sensitive elements in or on the surface. The out put from each element may be received by a computer.

The shape of the surface used in the methods of the invention may be additionally or alternatively modified or adapted to assist the binding of beads to the molecules attached at each position or pixel and to allow a sensitive and accurate method. Hence, the surface may be modified or adapted, for example shaped, to allow the binding of one or more beads at each position.

Alternatively, the surface may be flat to optimise binding of molecules thereto.

Therefore, the surface may be contoured to allow the association or binding of one or more beads with each light sensitive element. Individual recesses may be associated with or located by each light sensitive element or groups of light sensitive elements which allow the beads to attach and to be associated with a single or individual light sensitive element or group of light sensitive elements on the surface. The recesses may allow the bead to be positioned only over a single element and to prevent movement of the bead over more than one light sensitive element or group of light sensitive elements.

Alternatively, each light sensitive element or group of light sensitive elements may be surrounded by a barrier to enable bead attachment and association with only that light sensitive element or group of light sensitive elements. Hence, barriers or obstacles may be placed on the surface around the one or more light sensitive elements.

A combination of recesses and barriers may also be used on a surface. Typically, the light sensitive elements which will have a molecule attached thereto will be adapted to have a recess or barrier associated therewith. One or more elements on a surface may be adapted, although typically all of the elements may be adapted e.g. to have recesses and/or barriers associated therewith.

The adaptation of the surface in this way e.g. the use of recesses and/or barriers allows a more sensitive and accurate method and may help to eliminate false positive results.

In a particular embodiment, the surface is adapted to allow the binding of a single bead at each position. Each light sensitive element or light sensitive element group and its surrounding barrier or recess may therefore be of a suitable size to bind an individual bead. The light sensitive element and/or barrier/recess may therefore be adapted to suit any particular bead size used with the surface. The surface may be adapted using techniques well known in the art, for example using photoresist.

The molecule is detected in the method of the invention by the presence and attachment of a bead. The beads are generally spherical and although the size of the beads is not critical as discussed above, they may for example be of the order of diameter of at least 0.5, 1, 1.5, 2, 2.5, 3 or 3.5 µm to allow the detection of single molecules and have a maximum diameter of not more than 10, 8 or 6 µm. Particularly, beads of 1 or 2.8 or 4.5 or 10 µm may be used in the present invention. By diameter is meant size along the longest axis of the bead or along any axis of a spherical bead.

Monodisperse beads, that is those which are substantially uniform in size (e.g. size having a diameter standard deviation of less than 5%) are preferably used as they provide very uniform reproducibility of reaction.

Non-magnetic polymer beads suitable for use in the method of the invention are available from Invitrogen as well as from QIAGEN®, SEROTEC®, MERCK®, PROMEGA®, to name a few. Non-magnetic beads may be manufactured from many different materials well known in the art, for example from plastic e.g. from polystyrene.

However, to aid manipulation and separation, magnetic beads are preferred. The term "magnetic" as used herein means that the bead is capable of having a magnetic moment imparted to it when placed in a magnetic field and thus is displaceable under the action of that field. In other words, magnetic beads may readily be removed by magnetic aggregation which provides a quick, simple and efficient way of separating any unattached beads following incubation of beads with molecules or with the surface. As previously described, this provides a distinct advantage over the fluorophores or chemiluminescence used in such methods in the prior art.

Thus, the magnetic particles which are unbound to the molecule attached to the surface may be removed onto a suitable surface by application of a magnetic field e.g. using a permanent magnet.

Magnetic beads comprise magnetically responsive material which responds to a magnetic field, for example, paramagnetic materials, ferromagnetic materials, ferrimagnetic materials and metamagnetic materials. Hence, iron, nickel and cobalt as well as metal oxides such as $Fe_3O_4$, $BaFe_{12}O_{19}$, $CoO$, $NiO$, $Mn_2O_3$, $Cr_2O_3$ and CoMnP can be used. The magnetically responsive material may be only one component of the bead, whose remainder may consist of a polymeric material to which the magnetically responsive material is affixed.

The quantity of magnetically responsive material in the bead is not critical and can vary over a wide range, for example, from about 1% to about 75% by weight of the particle as a whole. The range may be from 2% to 50%, form 3% to 25% or from 5% to 15%. The magnetically responsive material can be dispersed throughout the polymer, applied as a coating on the polymer surface or incorporated or fixed in any other manner that secures the magnetically responsive material to the polymer. Hence, the magnetically responsive material may form the nucleus or core of the bead.

The polymeric material that forms the remainder of the bead can be any material that can be formed into a solid bead. Examples of suitable polymers are polyesters, polyethers, polyolefins, polyalkylene oxides, polyamides, polyurethanes, polysaccharides, celluloses and polyisoprenes. Crosslinking is useful in many polymers for imparting structural integrity and rigidity to the bead.

Superparamagnetic beads for example those described by Sintef in EP-A-106873 can also be used which allow the avoidance of magnetic aggregation and clumping of the beads even with high permeability. Further, the magnetic particles sold by Invitrogen as DynaBeads are particularly suited to use in the present invention.

A particular advantage of using magnetic beads is that the beads can be "pulled down" on to the surface of the chip by a magnet, to aid in the detection of the beads. This is a particular advantage for the detection of single molecules using the methods.

The bead may be attached to the molecule either directly or indirectly in any convenient way, before or after attaching the molecule to the surface, according to techniques well known in the art and described in the literature.

Thus the molecule may be attached directly to the beads. Such attachment may readily be achieved by methods (e.g. coupling chemistries) well known in the art and conveniently the molecule may be bound directly to the bead for example by coating.

Alternatively, the bead may be indirectly attached to the molecule. The molecule may therefore be bound to the bead through one or more other molecules which may be directly bound to the bead. The molecule may be bound to one or more linking moieties or spacers which are bound to the bead and which have an affinity for the molecule or for a tag incorporated into the molecule. Particularly, the molecule may be attached to the bead by biotin/streptavidin binding or by biotin/avidin binding. Hence, streptavidin or avidin coated beads may be used to bind a molecule which is linked to a biotin group.

In one aspect, the molecule may be attached to the bead prior to attachment of the molecule to the surface. In this aspect, a single or multiple copies of the molecule may be bound onto each bead.

Alternatively, the molecule may first be brought into contact with the surface before being attached to the bead. In this case, the bead may conveniently carry or be provided with a binding moiety capable of binding to the molecule. Such binding moieties are well known in the art e.g. biotin/streptavidin may be used where the molecule is coupled to a biotin group and the beads are streptavidin coated or the bead may carry an antibody which binds to the molecule.

Preferably, the bead is attached to the surface by a covalent bond. Particularly, the bead may be ligated to the molecule or incorporated into the molecule by a polymerase reaction.

In a further aspect of the invention, coloured transparent beads can be used in the methods and can be detected by the surface. One or more different beads of different colours can be used as labels. Therefore, two, three or four different bead colours can be used in the method of the invention. Particularly, one or more different bead colours can be used simultaneously and can be detected by the surface. In this embodiment, it is possible to detect different bead colours and hence different bead labels attached to a surface. Different bead colours can be used to detect different molecules on the surface, for example, without their position being predetermined. Hence, a specific bead colour may specifically bind to a molecule attached to the surface. Coloured beads may be produced by marking e.g. coating such beads with a dye e.g. a fluorescent dye. Further, beads of different colour intensities may be used.

Further, different size beads can be used as labels. Beads of 2, 3, 4, 5, 6, 7, 8, 9 or 10 different sizes can be used simultaneously as labels and be detected by the surface. Beads of different sizes will therefore also be able to be used to detect a molecule without knowing its location on a surface.

It may be possible to multiplex this method further by using combinations of different bead sizes, colours and/or intensities. Hence, different subgroups of beads which may be a range of colours, colour intensities and/or sizes may be used in the methods. It may be preferable, where multiple bead parameters are to be measured for the surface to comprise magnetic detection elements e.g. Hall elements in addition to the light sensitive elements. Hence, in this instance, magnetic beads could be employed, whose size could be detected by the magnetic detection elements and whose colour could be detected by the light sensitive elements. The magnetic detection elements may be stacked on top or below or may be adjacent to each light sensitive element. Using different beads colours for each size bead can increase the number of molecules which can be identified in this way without a predetermined location being necessary.

The bead may also be removable from the molecule to which it is bound. A cleavage site may be placed at any position between the surface and the bead i.e. at any place in any of the molecules bound to the surface and/or to the bead. Particularly, a restriction enzyme site may be incorporated between the bead and the molecule. Any restriction enzyme site may be used and cleavage may then be achieved using any suitable restriction enzyme for that site. Particularly, a Type II restriction endonuclease may be employed. The restriction or cleavage site may be positioned directly adjacent to the molecule (i.e. at the end of the molecule most proximal to the bead) to enable the cleavage of the bead together with any linker or other binding moiety which may be present or the restriction or cleavage site may be positioned directly adjacent to the bead to enable cleavage of the bead. In this aspect, it may be possible to remove the beads for subsequent use or to strip the surface or image chip for reuse. In a further aspect, the molecule could comprise a restriction enzyme site at both ends, allowing complete stripping of the surface and the reuse of the bead. If the bead is incorporated into the molecule by ligation, a nicking restriction enzyme can be used to release the bead.

The term "molecule" as used herein generally refers to any molecule which can be detected using conventional microarray technology or other standard detection techniques known in the art. In particular, the molecule to be detected can be a nucleic acid molecule e.g. DNA, RNA, or a part thereof, a protein, polypeptide or peptide, an antibody or a chemical compound.

The molecule to be detected may be defined as a "target molecule".

The target molecule may be directly or indirectly attached to the surface.

A target molecule which is indirectly attached to the surface may be attached through a capture molecule which is attached to the surface. Alternatively, a target molecule which is indirectly attached to the surface may be comprised within a larger molecule or entity which is attached to the surface i.e. it may be part of another molecule and may be detected by a detector molecule. Hence the target molecule can be comprised in another molecule or entity.

A target molecule directly attached to the surface may be chemically coupled thereto.

A "capture molecule" is a binding partner for the target molecule, which binds to and has an affinity for the target molecule (e.g. specifically binds to or has a high affinity for the target). The capture and target molecule are therefore binding partners, preferably specific binding partners where the capture molecule will only bind to the target molecule, allowing detection and identification of the target molecule. Several different capture molecules may therefore have binding affinity for one target molecule type and the surface may have one or more capture molecule types present for each target molecule type.

A detector molecule is a molecule which may bind to the target molecule (e.g. which may be present within a larger molecule) and which again may have an affinity for the target molecule. Hence, the detector may bind specifically to the target molecule or may be capable of becoming incorporated within a molecule.

If the target molecule is a nucleic acid molecule e.g. DNA or RNA, or a part thereof, the corresponding capture or detector molecule may be a complementary nucleic acid sequence (e.g. DNA, RNA or a part thereof) to the nucleic acid sequence of the target molecule. In this instance, the capture or detector molecule may be a complementary fragment of the target molecule sequence e.g. may be between 1-200 nucleotides in length e.g. at least 10, 20, 30, 40, 50, 60, 70, 80, 90, 100, 120, 140, 160, 180 or 200 nucleotides in length. Alternatively viewed, the capture or detector molecule may be an oligonucleotide which is single stranded and may be synthetic.

If the target molecule is a protein, polypeptide or peptide, the capture or detector molecule could be an antibody which specifically binds to the target molecule or a fragment thereof or may be a ligand for the target protein, polypeptide or peptide e.g. cells (bacterial, mammalian or other cell types) or viruses can be detected by detecting a target protein on the cell or viral surface or in the cell if a cell lysate is applied.

Further, if the target molecule is an antibody, the capture or detector molecule may be a protein, to which the antibody will bind.

Antibodies which can be used as binding partners or capture/detector molecules in the method of the present invention may be of any species, class or subtype. Furthermore the antibody may be natural, derivatised or synthetic. Representative "antibodies" thus include:

a) any of the various classes of sub-classes of immunoglobulin, e.g. IgG, IgA, IgM, IgD or IgE dervied from any animal e.g. any of the animals conventionally used e.g. sheep, rabbits, goats or mice, b) monoclonal or polyclonal antibodies c) intact antibodies or fragments of antibodies, monoclonal or polyclonal, the fragments being those which contain the binding region of the antibody, e.g. fragments devoid of the Fc portion (e.g. Fab, Fab', F(ab')2, Fv), the so called "half molecule" fragments obtained by reductive cleavage of the disulphide bonds connecting the heavy chain components in the intact antibody d) antibodies produced or modified by recombinant DNA or other synthetic techniques, including monoclonal antibodies, fragments of antibodies, "humanised antibodies", chimeric antibodies or synthetically made or altered antibody-like structures. Also included are functional derivatives or "equivalents" of antibodies e.g. single chain antibodies, CDR-grafted antibodies, minimum recognition unit antibodies etc.

The target molecule may be indirectly attached to the surface through a capture molecule. In this aspect, a sample comprising the target may be applied to the surface which may have one or more capture molecules arranged thereon. The capture molecules in this aspect may be nucleic acid molecules e.g. DNA, RNA or protein, polypeptides or peptides, antibodies or fragments thereof or chemical compounds and which may allow the binding or attachment of the target molecule. In this aspect, the invention therefore provides a method of detecting a target molecule attached to a surface having one or more capture molecules arranged thereon the method comprising detecting said target molecule by detecting a bead attached to said target molecule wherein said surface is provided with one or more light sensitive elements and wherein each light sensitive element is arranged to detect a bead adjacent thereto.

Particularly, the method may include a further step of applying a sample comprising a target molecule to the surface. If the target molecule is not pre-labelled with the bead before being applied to the surface, a further additional step can be carried out after applying the sample comprising the target molecule to the surface of adding the beads to the surface.

As previously described, a removal step of the unbound beads may additionally be carried out.

This particular aspect of the present invention has several different applications in research and diagnostics. For example, the method can be used in gene expression studies. In this aspect, the surface would be prepared with an array of nucleic acid capture molecules attached, complementary to and representative of the target molecules which are to be analysed. Usually, DNA oligonucleotide capture molecules may be employed and the target sample would be a cDNA or cRNA sample which would be added to the surface with attached capture molecules under conditions of high stringency. As previously described, the target sample could be labelled with beads before or after addition to the surface.

In this aspect, each DNA oligonucleotide would usually have a predetermined position on the surface and the presence of the target would be determined by virtue of the detection of one or more beads at that position. Expression levels of any given gene could be detected with such a method. Particularly, it would be possible to detect the presence of single molecules in a sample. In this instance for single molecule detection it may be preferable to reduce the ambient temperature and/or to increase the number of hybridised base pairs. Alternatively, for the detection of single DNA molecules ligation of the target to the capture molecule (or detector molecule) in the below embodiments may be advantageous, by making the target (or detector) molecule a double stranded DNA with an overhang or by making a nick between a single stranded capture molecule (or a single stranded detector molecule) ligate to a single stranded target molecule.

The method as described above could also be employed in comparative genome hybridisation assays to detect, for example, chromosome deletions or aneuploidy in a sample.

Further, the method could be used to detect the presence of a microorganism such as a bacterium or virus or detect the presence of a particular cell type e.g. a cell from a particular tissue.

The target molecule may also be indirectly attached to the surface as part of a larger molecule or entity which is directly attached to the surface. In this way part of a molecule can be detected by the addition of detector molecules which specifically bind to the target molecule.

It is also possible that the molecule to be detected (target molecule) is directly attached to the surface (i.e. is itself directly arranged on the surface). Therefore, the target molecule in this embodiment is not attached to the surface through a capture molecule as described previously but may instead be attached by chemical coupling e.g. through a thiol group or any other group which allows direct attachment to the surface e.g. through an adapter molecule. The surface can therefore have one or more target molecules arranged thereon. In this instance, it is possible to detect the target molecules by their attachment to detector molecules which may be added to the surface. This can be considered as a type of "inverse array". Hence, the detector molecules can be bead labelled (for example, detector molecules can be spread over the bead surface) and the target molecules detected by the presence of the bead being indirectly bound to the target molecule through the bound detector molecule.

The inverse array aspect of the present invention is extremely advantageous and allows the detection of single molecules using a universal array surface, rather than one which has been prepared with capture molecules (or probes) designed specifically to bind to particular target molecules.

Thus, the fact that arrays usually need to be prepared before the addition of a sample comprising target molecules is a disadvantage of microarray technology in general. The preparation of microarrays is laborious and demands special and expensive equipment where the selection of capture molecules for particular targets is carried out at the preparation stage. Further, such arrays may provide unreliable quantitative results. The use of an inverse array of the present invention addresses many problems of the art, particularly with respect to detecting single molecules.

Thus, the inverse array aspect is a preferred embodiment of the invention for many reasons in addition to the ability to detect single target molecules. There is no preparation of the array with pre-selected capture molecules and a universally prepared array is used where detector molecules are supplied at use. In this respect, target molecules present in a sample are first distributed on the array surface and are allowed to bind to the surface at random. The surface of the array may then be washed and detector molecules added. The detector molecules may be either labelled with beads upon addition to the array or bead labels may be subsequently added after detector molecule application and binding has occurred. Methods of attaching beads to molecules are already described herein and these methods and comments apply to the inverse array aspect.

Where more than one target molecule is to be detected on the inverse array, a different bead label may be used for each target to be detected. Thus, a particular detector molecule specific for a particular target molecule will be labelled with a particular bead. Each detector molecule specific for each target molecule will be labelled with a different bead e.g. a different bead colour, allowing the detection of more than one target molecule on the inverse array. Alternatively, particular detector molecules for each target molecule may be added one at a time to the array and then removed after the target molecule has been detected (or not). In this aspect, the different detector molecules are therefore added separately and sequentially to each other.

The inverse array is capable of detecting single molecules. As described previously, single molecules can be detected by the use of bead labels which correspond to the size of the elements which are used for detection. Thus, in the context of the inverse array, particular bead sizes are also selected which are large enough to detect the presence of a single molecule.

However, this aspect is not limited to detection by a surface provided with one or more light sensitive element (although such a surface is preferably used) and any detection method may be employed which can detect the presence of a single bead and thus a single molecule.

The detection of the bead label for an inverse array may be optical, magnetic, electric or electrochemical and particularly the detection of the bead may be carried out using an apparatus comprising a surface which is provided with a means for detecting a bead. The surface may therefore comprise one or more elements which provide an output dependent on the presence or absence of a bead. The surface may provide one or more light sensitive elements as described previously or more provide other elements instead of or in conjunction with light sensitive elements which are capable of detecting a bead, e.g. Hall elements or giant magnetoresistive (GMR) sensors. As discussed previously, the one or more elements on the surface are capable of outputting a signal which is dependent on the presence or absence of a bead and the bead is thus directly detected by the surface.

In order to detect single target molecules in the inverse array method, the bead label selected preferably has a size (diameter) which corresponds to the size (width and/or breadth or diameter) of the one or more elements provided by the surface as described in detail previously.

Thus, the invention provides a method of detecting a target molecule attached to a surface, the method comprising the steps of i) binding a target molecule to a surface ii) adding a detector molecule to the surface wherein said detector molecule is either attached to a bead or is labelled with a bead after addition to the surface and iii) detecting the presence of said bead attached to said target molecule, wherein said surface is provided with one or more elements capable of detecting a bead, wherein each element is arranged to detect a bead adjacent thereto and wherein said bead is either of a size which corresponds to the size of said one or more elements or is at least 1 µm in diameter, allowing the detecting of a single target molecule attached to the surface.

A further aspect allows the quality control of the surface having one or more molecules arranged thereon. In this instance, the target molecules to be detected are those arranged on the surface. These molecules may be detected e.g. for the purpose of ensuring the presence of the molecules on the surface prior to using the surface in subsequent detection methods, by the binding of bead labels indirectly or directly to the molecules, i.e. either through the binding of a further target or capture/detector molecule or not through the binding of a further target or capture/detector molecule. The detection of beads and hence the arranged molecules therefore allows a method of quality control for the surface production. The beads may be removed from the surface by cleavage e.g. using restriction enzymes as discussed previously.

The invention may thus provide a method of detecting a target molecule attached to a surface having one or more molecules arranged thereon the method comprising detecting said target molecule by detecting a bead attached to a capture/detector or target molecule wherein said surface is provided with one or more light sensitive elements and wherein each light sensitive element is arranged to detect a bead adjacent thereto.

As briefly discussed above, the molecules attached directly to the surface may be bound through a thiol, digoxigen or amino group or any other molecule or adaptor that allows binding to the surface. Molecules can be attached to surfaces e.g. to chips and image chips by techniques which are well known in the art.

One or more molecules may be attached to the surface. Hence, the method can be used to detect one or more different types of target molecule depending on the number or type of molecules arranged on the surface. Particularly, more than one molecule type may be detected e.g. at least 10, 100, 200, 500, 1000, 5000, 10000, 50000, 100000 or more molecule types may be detected. As previously discussed, the method is capable of detecting a single molecule of each molecule type. Typically, the maximum number of different molecule types that can be detected is at least 5, 10, 15, 20, 25, 30, 35 or 37% of the number of light sensitive elements present on the surface. When more than one molecule is arranged on the surface, an array of molecules can be said to be present or arranged. As described previously, typically, each molecule will be associated with a light sensitive element or a group of light sensitive elements to allow detection of the attached bead by the light sensitive element.

When more than one molecule is arranged on a surface, each molecule may be placed at a single predetermined position on the surface. In one aspect therefore, the position of all molecules on the surface may be known. In this respect, it is possible to relate the position of bead binding to the position of a particular molecule on the surface and to identify the presence or absence of a target molecule.

However, if different bead labels are employed to detect particular molecules, it may not be necessary for the molecules to have predetermined positions. In this aspect, the molecule can be detected by the type of bead attached thereto. As described previously, different bead colours or colour intensities or sizes can be used to detect more than one different molecule and combining beads of different sizes and colours or colour intensities can provide a multiplex method for the detection of many different molecules.

Each molecule attached to the surface may be present as a single molecule or multiple copies may be present at each position. As discussed above, it is possible to detect single molecules using the method of the invention and hence, single molecules attached to the surface may be detected by the binding of a bead. Alternatively, multiple molecules may be arranged on the surface at each position. If multiple molecules are attached, it may be possible to detect the quantity of molecules i.e. by detecting the number of attached beads.

The surface may also comprise one or more molecules which act as a control for the method e.g. nucleic acids can be included which are of randomised sequence to control for non-specific binding.

The invention further provides an apparatus for use in the methods described above. Specifically, the invention provides an apparatus for detecting the presence of a molecule having a bead attached thereto comprising a surface which is provided with a means for detecting a bead wherein the shape of said surface is configured to receive and retain a bead.

Particularly, the apparatus may comprise a surface which further has one or more molecules attached thereto and associated with one or more of said means for detecting said beads.

The surface preferably comprises one or more elements which provide an output dependent on the presence or absence of a bead. In a preferred aspect, an apparatus is provided comprising a surface which has one or more light sensitive elements wherein said surface is adapted to receive a bead at said one or more light sensitive elements.

Particularly, the surface shape is configured to enable each element (particularly each light sensitive element) to receive and retain a bead and recesses and/or barriers may be associated with or located at each element or group of elements to allow beads to attach and to be associated with an individual element or group of elements on the surface. As described above, one or more of the elements or group of elements may be associated with a recess and/or barrier on the surface.

In a preferred embodiment, the surface is configured to allow the attachment and retention of a single bead to an element for the detection of a single molecule. The recesses or barriers may therefore be designed depending on the size of bead to be used on the surface and the size of the element. The recess/barrier may be sized so that only a single bead will be attached to each element.

The apparatus may comprise further modifications for use in the methods of the invention. For example, the surface may be coated with gold to enable the binding of molecules e.g. of DNA to the surface, or the surface may be subject to silanisation or digoxigenation.

A further embodiment of the invention provides an apparatus for detecting the presence of a molecule having a bead attached thereto said apparatus comprising a surface which is provided with one or more light sensitive elements, and a light source illuminating said light sensitive elements, whereby each light sensitive element is arranged to detect a bead adjacent thereto by detecting a consequent change in light intensity.

Additionally, the invention provides an apparatus for detecting the presence of a molecule having a bead attached thereto comprising a flow cell and a surface which is provided with one or more light sensitive elements wherein each light sensitive element is arranged to detect a bead adjacent thereto. Particularly, the flow cell allows the application and removal of a sample and/or beads to the surface. Hence, the flow cell allows molecules and/or beads to be deposited on or to flow across the surface in solution. This embodiment may further be arranged in use with a visible light source.

The apparatuses of the invention may further be formed as described above e.g. the surface may be adapted to enable each light sensitive element to receive a bead and/or may be coated with gold. Additionally, the apparatuses of the invention may be associated with a reader which can detect and read the signal outputs from the individual light sensitive elements. The reader can consist of a circuit board linked up to a computer.

The invention also provides for the use of the apparatus for the detection of a bead.

The apparatus described above has many further uses other than in the specific molecule detection methods discussed previously.

It is possible to use the apparatus for the identification of beads e.g. to check the quality of beads for example to check whether beads produced are of a spectrum of different sizes. In this aspect, the beads are applied to the apparatus and the amount of light detected by each light sensitive element can be determined. Differences in the amount of light received at different light sensitive elements may indicate that a bead population is not of uniform size. This use is most preferably carried out using the apparatus which is adapted to receive a single bead at each light sensitive element.

Further, fluorophores attached to a bead may be identified using the apparatus described above. This may facilitate the identification of molecules attached to the bead which are coupled to the fluorophores. In this aspect, different fluorophores attached to a bead may be detected, e.g. 1, 2, 3 or 4 different fluorophores may be detected. In this use, the bead may be tethered to the surface using a polymer, for example a nucleic acid molecule.

Additionally, the apparatus can be used to determine the characteristics of a molecule. A DNA molecule for example could be tethered to the surface and the length of the DNA molecule could be determined by the signal received from binding the bead. A short DNA molecule would result in the bead being closely associated with the surface, but a longer DNA molecule would result in the bead being more distal from the surface which would in turn effect the output generated by the surface. Further, a magnetic field gradient may be applied in the direction along the surface. In this way, long DNA molecules may be measured by the number of light sensitive elements covered.

The invention further provides the use of an apparatus comprising a surface provided with one or more light sensitive elements for the detection of a bead.

More particularly the invention provides a use of an apparatus comprising a surface provided with one or more light sensitive elements for detecting a single molecule wherein said single molecule is attached to said surface and labelled with a bead which is of a size corresponding to the size of said one or more light sensitive elements and said single molecule is detected by the detection of said bead.

A kit is also encompassed comprising the apparatus as defined above. The kit may further comprise beads which are suitable for use with the apparatus i.e. which are capable of binding to the surface. Alternatively, the kit may comprise i) a surface which is provided with one or more light sensitive elements and ii) one or more beads which are capable of being detected by the surface. The beads may also preferably have a size corresponding to the size of one or more of the light sensitive elements. The kits may further comprise enzymes e.g. restriction enzymes for cleavage of the beads and/or oligonucleotides.

Referring to the Figures, a schematic of the method of the invention can be seen in FIG. 1. Hence, the molecule to be detected 2 (DNA) is attached to the surface 4 which is a Micron MT9T001 (APTINA™) 3 Mpixel CMOS digital image sensor. The image sensor is prepared as discussed below by soldering onto a printed circuit board and removing the protective glass from the image sensor using a diamond cutter.

The DNA molecule 2 is attached to the image sensor 4 using the methodology discussed in detail further below.

Figure 5:
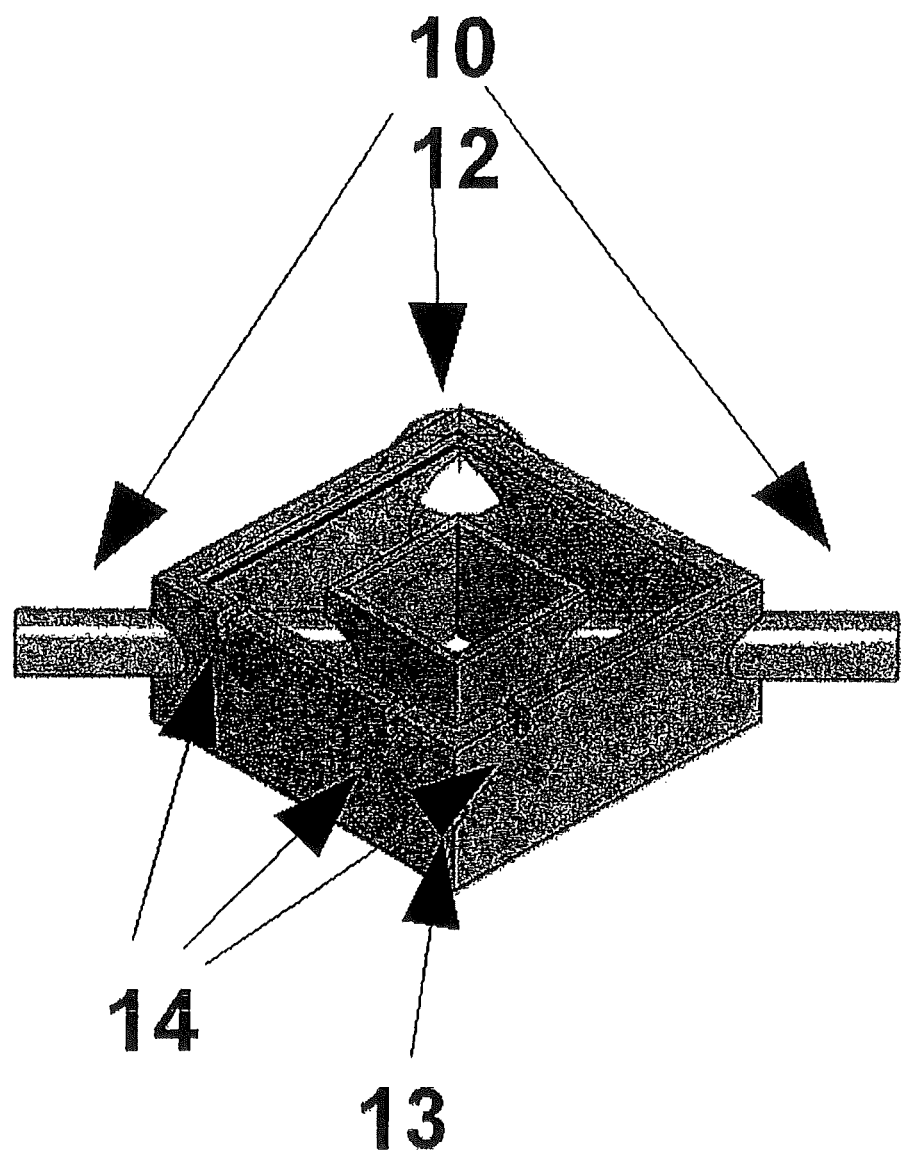
FIG. 5 shows a "3d-printed" unit to be placed upon a packaged image chip to produce a flow cell.

A flow cell (see FIG. 5) is produced from plastic by 3D printing which fits the size of the image sensor and allows fluid flow to and from the active surface through an inlet and outlet 10 which can be connected by flexible plastic tubes. The flow cell is attached to the image sensor by applying a thin layer of epoxy glue to the edge of the image sensor and placing the flow cell on the sensor 4. A glass cover is placed on top of the flow cell and the outer compartment of the flow cell filled with epoxy glue to seal the inner compartment and to protect the outer compartment and wires.

The Micron MT9T001 (APTINA™) 3 Mpixel CMOS digital image sensor 4 is provided with a plurality of light sensitive elements 3. The DNA molecule 2 which is attached to the Micron MT9T001 (APTINA™) 3 Mpixel CMOS digital image sensor 4 is associated with a light sensitive element. In FIG. 1, only one DNA molecule 2 is associated with each light sensitive element 3 but as described previously, more than one molecule may be present.

A bead 1 (M280 Streptavidin bead from DYNAL®) is attached to the molecule (DNA) 2, (using the methodology discussed further below in detail) and can be detected by the corresponding light sensitive element 3 to which that molecule is bound. Hence, the beads are provided to the image sensor surface through the flow cell and will bind to the DNA molecules attached (in this instance through streptavidin on the bead surface binding biotin on the attached DNA molecule). The bound bead 1 will cast a shadow or obstruct light from reaching the light sensitive element 3 and can therefore be detected by the light sensitive element. This will result in the output of a signal by the light sensitive element which differs from that outputted when beads are absent. Hence, the light sensitive elements are arranged to output a signal dependent on receipt of light.

The signal from each light sensitive element is received by a computer or data processor which can process and store the data (see FIG. 6 discussed below) through a BLACK-FIN® control unit. A result from each light sensitive element is therefore produced. As can be seen in FIG. 1, a light source 9 is used to illuminate the apparatus during the method for example a lamp. Therefore, the molecule 2 is detected by the detection of the bead 1 attached to that molecule by virtue of the shadow the bead creates on a light sensitive element 3 provided by the surface 4.

Figure 2:
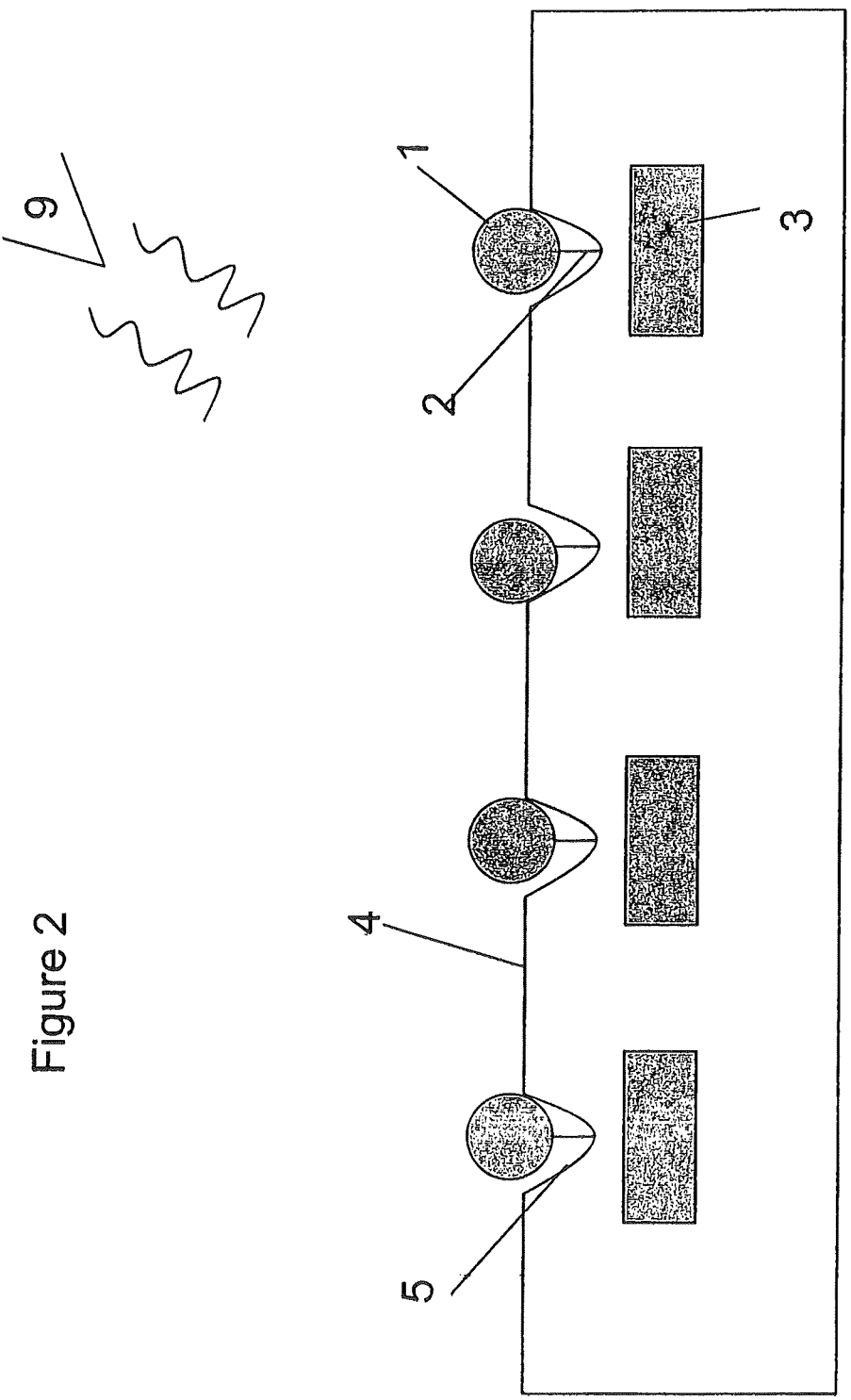
FIG. 2 shows a schematic view of the method using a configured surface of the invention.

In FIG. 2 the above method is again shown, where a DNA molecule 2 is attached to a surface 4 (a Micron MT9T001 (APTINA™ 3 Mpixel CMOS digital image sensor) which provides a plurality of light sensitive elements 3. The molecule to be detected is associated with a light sensitive element 3 provided by the Micron MT9T001 (APTINA™) 3 Mpixel CMOS digital image sensor 4 and beads 1 (M280 Streptavidin beads from DYNAL®) are attached to the molecule to be detected. Again, the bead is detected since it will obstruct light from reaching the light sensitive element which will result in the production of a different output from the element than that produced when beads are absent. In this embodiment, the surface is configured to receive and retain a bead and in this instance contains recesses 5. Each recess 5 is associated with a light sensitive element and allows the bead 1 which is bound to the molecule 2 to be specifically associated with only the light sensitive element to which the molecule is associated or attached. This prevents the bead from being detected by an adjacent light sensitive element and allows a more sensitive method to be used. In an alternative embodiment as described previously, the surface may be configured to receive and retain a bead by using barriers on the surface i.e. barriers around or associated with each light sensitive element.

Figure 3:
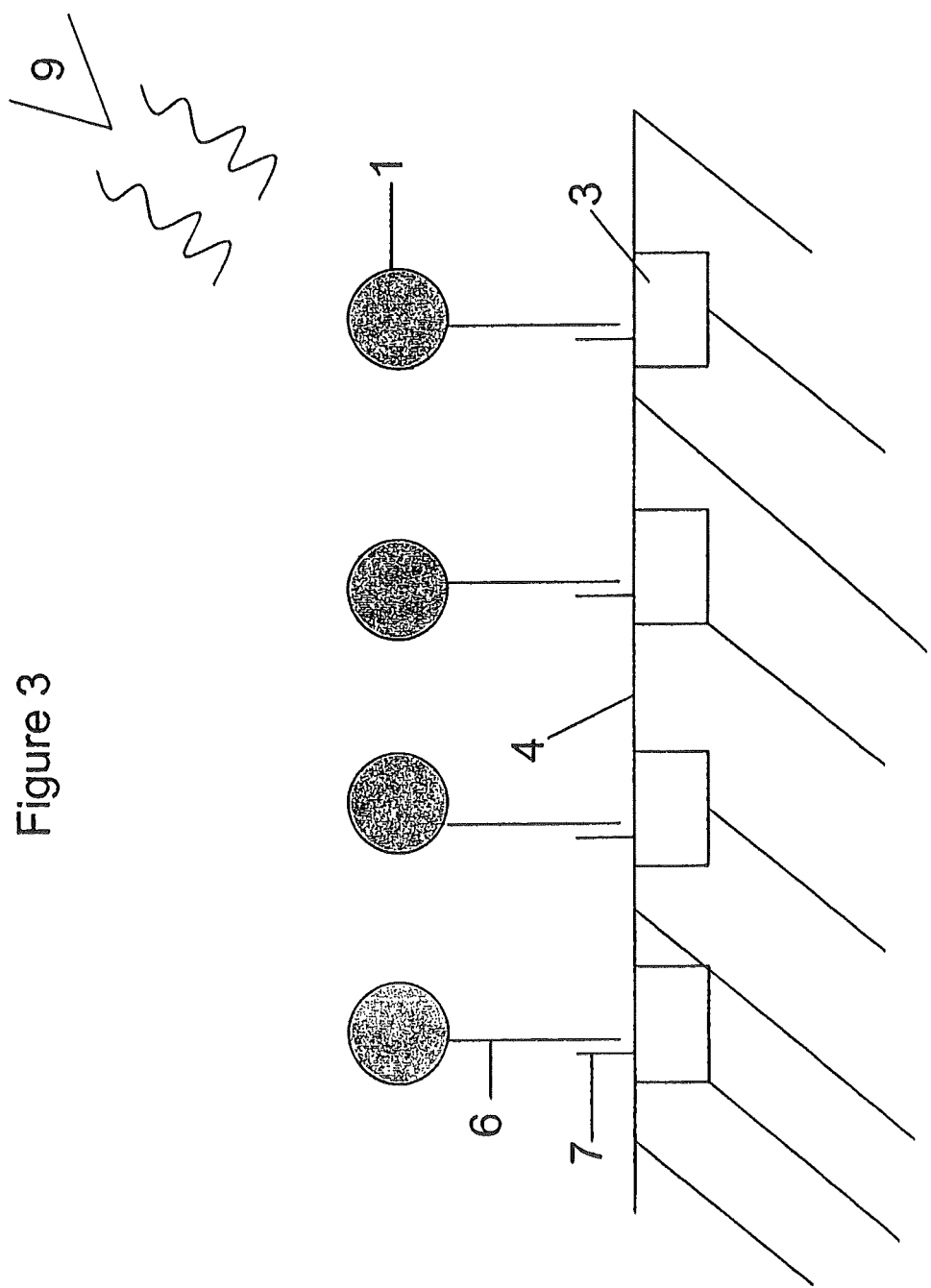
FIG. 3 shows a schematic view of the method where capture molecules are attached to the surface.

FIG. 3 demonstrates the method of the invention wherein the molecule to be detected or target molecule 6 (DNA molecule) is indirectly attached to the surface 4 (a Micron MT9T001 (APTINA™) 3 Mpixel CMOS digital image sensor). In this embodiment, the Micron MT9T001 (APTINA™) 3 Mpixel CMOS digital image sensor 4 provided with a plurality of light sensitive elements 3 has capture molecules 7 (complementary DNA molecules) attached to the surface which are specific binding partners for the target molecule 6. The capture molecules 7 are associated with the light sensitive elements on the surface 4 and in FIG. 3 a single capture molecule 7 is shown as being associated with each light sensitive element 3. However, more than one capture molecule may be present at any particular light sensitive element. A sample containing a target molecule 6 which will specifically bind to the capture molecule(s) 7 is applied to the surface 4. The target molecule 6 can be labelled with a bead 1 (M280 Streptavidin bead) before or after addition to the surface. Any unattached beads can be removed from the surface by use of for example a magnet if the beads are magnetic. The bead attached to the target molecule is detected by the light sensitive element to which it is associated by casting a shadow on that light sensitive element. As discussed previously, the surface can be illuminated with a light source 9 and the signal outputted by each light sensitive element which is dependent on the presence or absence of a bead can be read by a computer or data processor. The capture molecule(s) at each position may be the same or different and hence different target molecules can be detected by the method as described above.

Figure 4:
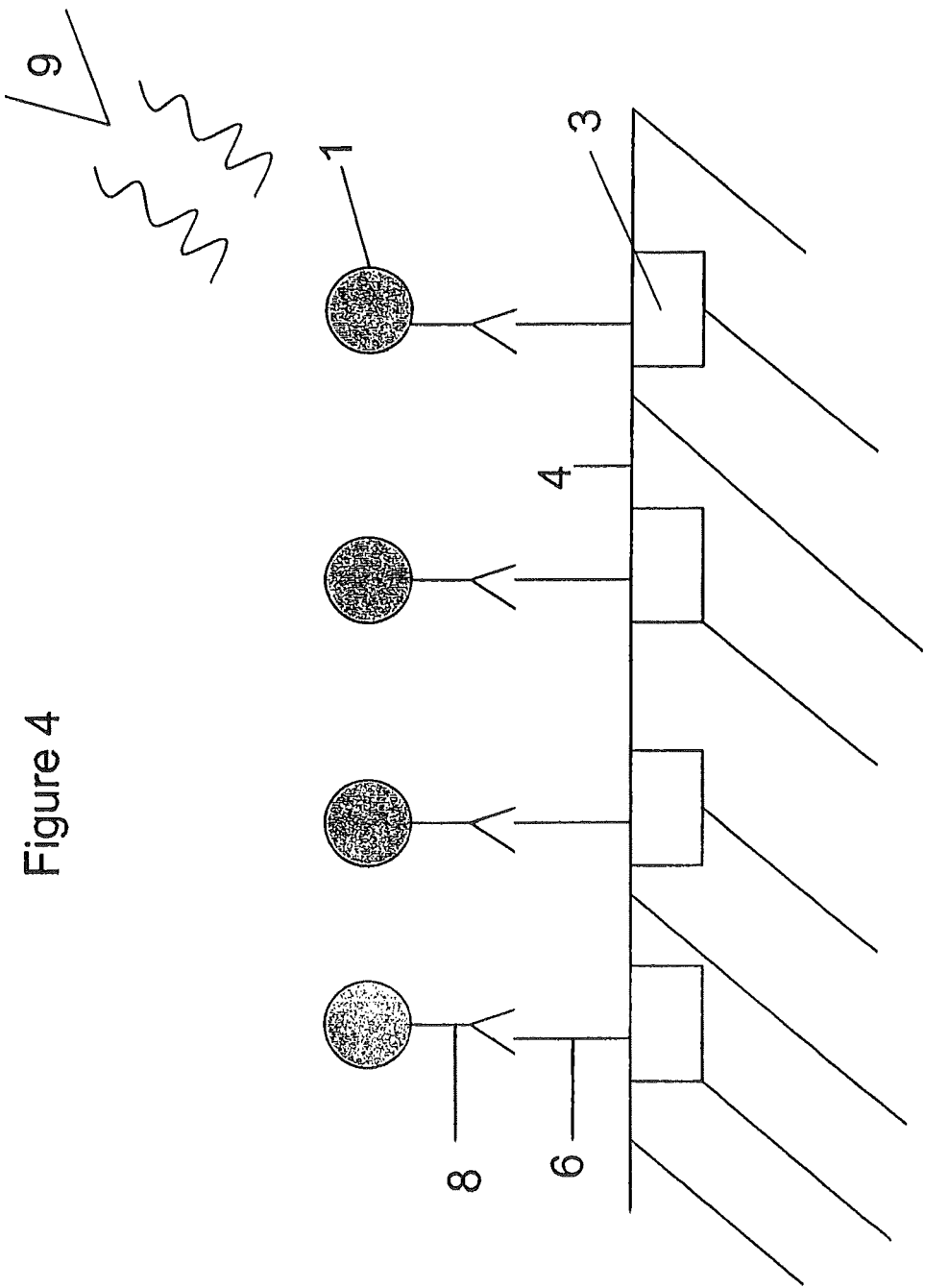
FIG. 4 shows a schematic view of the method where target molecules are attached to the surface.

The embodiment in FIG. 4 shows the surface 4 (a Micron MT9T001 (APTINA™) 3 Mpixel CMOS digital image sensor) having target molecules to be detected 6 e.g. DNA attached and associated with individual light sensitive elements 3. To detect the target molecules 6, detector molecules 8 (e.g. complementary DNA molecules) which bind to the target molecules are applied to the surface 4. The detector molecules 8 are attached to beads 1 (M280 Streptavidin beads), either before or after addition of the detector molecule to the surface, and the presence of the target molecule 6 is detected by the shadow cast by the bead on the light sensitive element 3 with which the target molecule 6 is associated. The signal outputted by the light sensitive element will differ dependent on the amount of light received by the element which is affected by the presence or absence of a bead. The surface will be illuminated as discussed previously by a light source 9 and the signals from each light sensitive element will be received by a computer or data processor which can process the data and produce results indicating the presence or absence of a bead and thus a target molecule at each light sensitive element.

Preparation of the Apparatus

One Chip Device Based on PLCC Packaged Chip

A Micron MT9T001 (APTINA™) 3 Mpixel CMOS digital image sensor is soldered onto a printed circuit board (PCB) and tested for functionality by connection to the BLACKFIN® microcontroller from Analog Devices a microcontroller using the PPI (parallel peripheral interface).

Preparation of Image Chip:

After soldering to the PCB, the protective glass is carefully removed from the CMOS digital image sensor by a diamond cutter, and the chip surface is cleaned by washing with pure ethanol. A flow-cell (FIG. 5) is produced from plastic by "3D printing" so that it fits with the size of the MT9T001 CMOS digital image sensor and allows fluid flow to and from the active surface through inlet and outlet (10) which can be connected via flexible plastic tubes.

A thin layer of epoxy glue is distributed on the edge e.g. by stamping it towards a thin layer of fluid glue. It is then placed upon the chip, and the epoxy was allowed to harden. For some of the chips, microlenses and BAYER filters are removed at this stage. A cover glass was placed on the top, covering both inner and outer compartments, and the outer compartment was filled up with epoxy glue through the inlet hole 12, letting air out through the outlet hole 13. The inner compartment is thereby sealed, and the outer area of the chip and all open bonding wires are protected. Optionally, a resistor network, together with an NTC resistor used as temperature sensor, could be fitted into the compartment before the cover glass was positioned. Electrical connections to the control circuitry will then be through connectors protruding through the cuts in the flow cell.

Removing Microlenses and BAYER Filters:

The microlenses and BAYER filters are removed by exposing the inner chamber to acetone for 15 minutes. Thereafter the upper layer is removed by careful scraping with a plastic toothpick.

Figure 6:
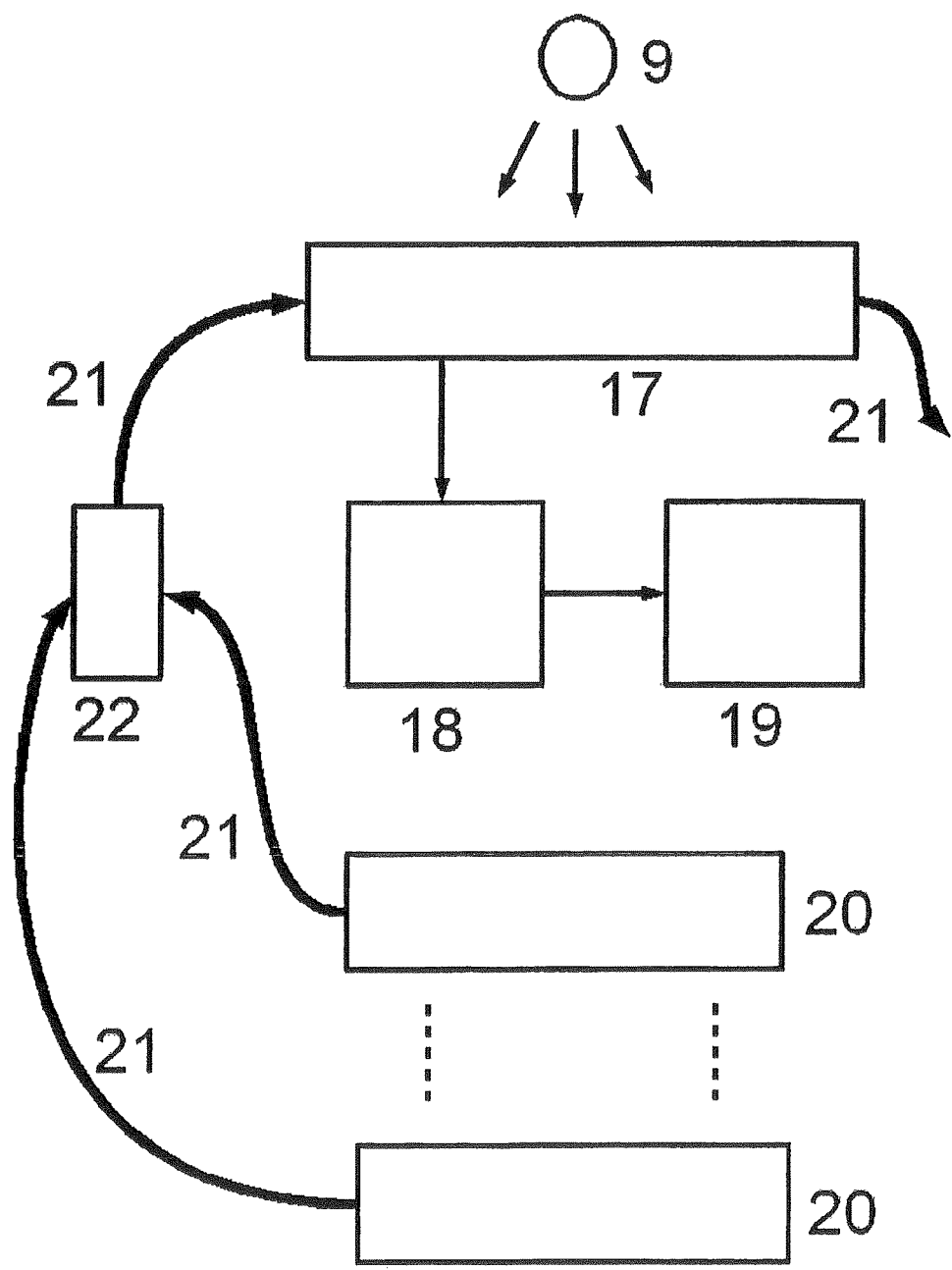
FIG. 6 shows a schematic view of the complete system.

Connection of Imaging Device to Controlling and Image Collection Units:

The imaging device 17 is connected as shown in FIG. 6. It is possible to capture images in the BLACKFIN® control unit 18 using hardware acceleration (direct memory access from image chip to RAM). Clock signal to the image chip could either be generated by a crystal or generated by BLACKFIN®. By using the uClinux™ distribution, the test program ppifcd_test which is distributed with the package, it is possible to capture to a RAM-disk file. This is described in the uClinux™ wild.

This file can then be transferred to a computer 19 over a network (if using a development board with an ethernet controller) by using NFS, tftp, ftp etc. or using USB.

Connection of Imaging Device to Fluid Supply Units:

The imaging device 17 is further connected to the fluid supply units as shown in FIG. 6. The fluid supply consists of a number of separate fluid containers 20 each equipped with its own pump or syringe to drive the fluid through the tubing 21 to the manifold 22 and further to the imaging device. Used fluid is discharged, e.g. into a container.

Mono or Multi-Chip Device Based on a Wafer (Bare Die)

Figure 7:
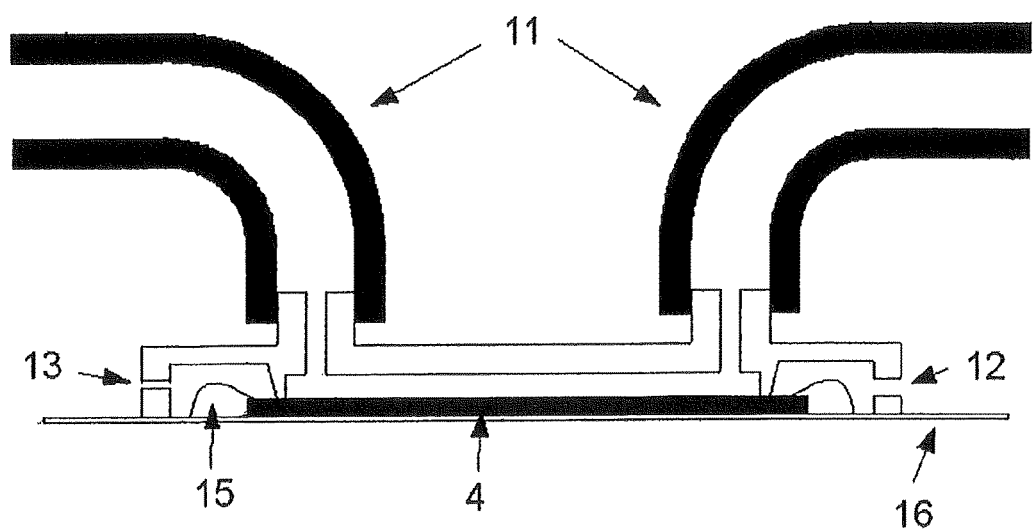
FIG. 7 shows a cross-section of a flow-cell placed upon a "bare die" image chip glued and bonded to a printed circuit board.

The wafer is removed from the normal production line before the Bayer filters and any other filters are equipped. Any preparation to enhance the polymer anchorage may now conveniently be performed, e.g. metallisation, using a mask that protects the connection islands. The wafer is tested and cut into chips in the normal way (bare die). FIG. 7 shows a mono-chip device, but any number of chips 4 can be fitted into the reaction chamber unit by gluing them into their exact positions on the board, using exactly fitted stakes that have been placed on the board 16, e.g. matching holes or "ears" in the corners of the reaction chamber unit (not shown in FIG. 7). The chips are connected to the board by Au wires through bonding 15. The reaction chamber unit is placed on top of the chip, guided by the stakes. It is then first glued to the chip or chips, and the enclosed volume containing the bonding connections is filled with epoxy through the inlet 12 while air is let out at the outlet 13 in FIG. 7. In multi-chip devices all the bonding connection volumes are interconnected.

In the mono-chip device, the single reaction volume is connected to the fluid supply and discharge units by plastic tubes, 11 in FIG. 7. In the multi-chip units, these volumes may be connected in different ways in series and/or parallel, either by external tubing or by channels in the unit. This may for small series production be produces in one unit by transparent plastic "3D printing", while for larger series, it may be produced e.g. from one plastic sheet with cavities at both sides and one flat, transparent sheet. The former may be produced from a flat sheet by milling or through moulding.

Protocol for Binding Beads to Image Chip Through DNA

DNA Preparation

From a pUC128 plasmid with an insert, a 1574 bp amplicon was amplified by

PCR using the following primers to make the following amplicons:

| 5' conjugation | Primer pair | amplicon product |
|---|---|---|
| Thiol (C-6) S-S | M13Rev:<br>5'-AGCGGATAACAA<br>TTTCACACAGGA-3' | BS-DNA |
| Biotin | Custom F:<br>5'-AAACGACGGCCA<br>GTGCCAAGC-3' | |

The purified amplicons were incubated in 10 mM of the reducing agent tris(2-carboxyethyl) phosphine (TCEP) in either 100 mM Tris-HCl pH 7.5 or NaPi buffer (0.1M $NaH_2PO_4$ pH 6.5 0.15M NaCl) and incubated for 2 hours. The amplicons were then purified by a biospin30 (BIO-RAD) column according to instruction manual, by eluting DNA with NaPi buffer. Then the DNA is diluted in NaPi buffer to a final concentration of 10 µg/ul. The purified amplicons were immediately applied to the imagechip, as described below.

Image Chip Functionalization:
1. The image chip is covered in a 5% solution volume/volume (3-Aminopropyl)triethoxysilane (CAS: 919-30-2) in dry acetone, 1 hr RT.
2. The image chip is then washed with acetone and incubated in 5 minutes. This acetone wash is repeated 3 times totally. Then the chip is rinsed in ethanol and then dried under $N_2$ gas
2. The image chip is incubated for 5 hours in a solution of 20 mM of the heterobifunctional linker m-Maleimido-benzoyl-N-hydroxysulfosuccinimide ester (s-MBS) solved in PBS (0.1M $NaH_2PO_4$, 0.15M NaCl, pH7.2) and incubated for 5 hours.
4. The image chip is then washed in PBS, then immersed in Deionized water then rinsed in ethanol rinsed and finally dried.

Attachment of DNA
1. DNA from "DNA preparation" protocol above is added to the imagechip and incubated for 5 hours.
2. The imagechip is washed with NaPi buffer 2 times, 5 min each on a shaker.
3. Then the image chip is incubated for 1 hour in 10 mM Mecaptoethanol in NaPi buffer.
4. The image chip is then washed for 5 min in NaPi buffer
5. The image chip is incubated in 1.5 M NaCl in 10 mM $NaH_2PO_4$ pH 7 for 10 min.
6. The image chip is washed in 5×SSC buffer (0.075M sodium citrate, 0.75M NaCl pH7.0) with 0.1% tween-20.
8. The image chip is rinsed in 5×SSC buffer
9. The image chip is stored in TE-buffer pH7.5 (10 mM Tris-HCl, 1 mM disodium EDTA Incubation of M-280 Streptavidin Beads from Dynal®
1. The beads are prepared as described in instruction manual in TE-buffer.
2. Beads are diluted to a final concentration of 1 µg/µl.
3. 10 µl of 1 µg/µl beads are added to the image chip and incubated for 30 minutes.

Appendix 1

PPI Frame Capture Device

The PPI frame capture device (PPIFCD) is a CMOS camera that connects to a BLACKFIN® via the parallel peripheral interface. It is intended to only capture single frames. Currently two camera sensors are supported.

See here: v4l_blackfin_camera for an v4l video driver supporting several sensors.

Micron MT9T001

The PPIFCD can be built using a Micron MT9T001 (datasheet) as described here It uses the standard Inter-IC Bus (intro) and the programmable flags to control the camera (e.g., to take out of standby mode, etc.).

Programs that Use the PPIFCD ppifcd_test

As mentioned here, the PPIFCD Frame Capture Driver test application aims to see if the digital image sensor can take pictures effectively which is connected through the PPI port to the target board. It records the row_time, total_frame_time, total_frame_capture_time, and the taken picture. If the printed data is as expected, the case passes, otherwise it fails.

fcd

This program serves CGI-based web pages that allow the user to specify settings, capture frames, and verify the overall operation of the camera.

Configuring the uClinux™ Kernel

The BLACKFIN® PPI supports a number of daughter cards, the PPIFCD being one. However, the PPI Driver will conflict with the PPI Camera frame capture driver if both are enabled. You will see this in the kernel log (i.e., dmesg) when the PPI drivers try to register the same major number for the char device.

Below are some configuration settings for the BF533 and BF537 STAMP boards. To get either of the programs mentioned above built, specify the following:

under Customize Vendor/User Settings
==Select BLACKFIN® test programs
Enable PPIFCD test program
==Select Blackfin app programs==
Enable CGI based Test Application for the PPI Frame Capture Driver BF533-STAMP Board As described here, the BF533-STAMP board is known to work with the PPIFCD with the following settings:

under Customize Kernel Settings
==Select Device Drivers
==Select Character devices==
Enable [*] Blackfin BF53x Programmable Flags Driver
Enable [*] Blackfin BF5xx PPI Camera frame capture driver
[ ] Blackfin BF5xx PPI Driver
==Select I2C support==
Enable I2C support
Enable I2C device interface
Select I2C Hardware Bus support
  Enable Generic Blackfin and HHBF533/561 development board I2C support
  Select BFIN I2C SDA/SCL Selection
    set (2) SDA is PF[0:15]
    set (1) SCL is PF[0:15]

BF537-STAMP Board

The BF537 has a built-in two wire interface peripheral and unlike the BF333 does not require the generic I2C support that is described here.

under Customize Kernel Settings
==Select Device Drivers
==Select Character devices==
Enable [*] Blackfin BF53x Programmable Flags Driver
Enable [*] Blackfin BF5xx PPI Camera frame capture driver
[ ] Blackfin BF5xx PPI Driver
==Select I2C support==
Enable I2C support
Enable I2C device interface
Select I2C Hardware Bus support
  Enable Blackfin TWI I2C support

The invention claimed is:

1. A method of detecting a single molecule attached to a surface with one or more light sensitive elements on or comprised within said surface wherein said surface is present in a photodetector without microlens and without filter layers, the method comprising:
   illuminating said one or more light sensitive elements with a light source,
   detecting a bead label attached to said single molecule
   said bead label (i) has a diameter which is at least 30% of the width, breadth or diameter of said one or more light sensitive elements or (ii) is at least 1 μm in diameter,
   said bead label and said surface are different entities,
   said bead label is detected by a reduction in the amount of light received by said one or more light sensitive elements caused by the presence of said bead label which blocks light from reaching the one or more light sensitive elements, and
   said single molecule is detected when the bead label is detected.

2. The method of claim 1, wherein said molecule is associated with said one or more light sensitive elements present in or on the surface.

3. The method of claim 2, wherein multiple molecules are associated with said one or more light sensitive elements but only one molecule type is associated with a light sensitive element.

4. The method of claim 1, wherein said surface is an image chip.

5. The method of claim 1, wherein said surface is coated with a layer of gold.

6. The method of claim 1, wherein said bead label is a magnetic bead.

7. The method of claim 1, wherein said single molecule attached to a surface is a target molecule, and wherein the method further comprises, prior to detecting, contacting the surface with a detector molecule, wherein said detector molecule is either attached to the bead label or is labelled with the bead label after addition to the surface.

8. The method of claim 1, wherein said bead label is directly detected by said one or more light sensitive elements.

9. The method of claim 1, wherein said single molecule attached to the surface is a target molecule and the bead is attached directly or indirectly to the target molecule.

10. The method of claim 1, wherein said single molecule attached to the surface is a target molecule and the target molecule is attached to the surface via a capture molecule which is attached to the surface.

* * * * *